United States Patent
Fukuda et al.

(10) Patent No.: US 8,354,527 B2
(45) Date of Patent: Jan. 15, 2013

(54) PROCESS FOR PRODUCING AMIDE OR LACTAM

(75) Inventors: Yasuhisa Fukuda, Ube (JP); Junichi Kugimoto, Ube (JP); Nobuhiro Il, Ube (JP)

(73) Assignee: Ube Industries, Ltd., Ube-shi (JP)

( * ) Notice: Subject to any disclaimer, the term of this patent is extended or adjusted under 35 U.S.C. 154(b) by 74 days.

(21) Appl. No.: 12/988,758

(22) PCT Filed: Apr. 22, 2009

(86) PCT No.: PCT/JP2009/058018
§ 371 (c)(1),
(2), (4) Date: Oct. 20, 2010

(87) PCT Pub. No.: WO2009/133801
PCT Pub. Date: Nov. 5, 2009

(65) Prior Publication Data
US 2011/0034687 A1   Feb. 10, 2011

(30) Foreign Application Priority Data

May 2, 2008 (JP) .................................. 2008-120431
Sep. 5, 2008 (JP) .................................. 2008-227669

(51) Int. Cl.
*C07D 201/04* (2006.01)
*C07D 225/02* (2006.01)
(52) U.S. Cl. ..................................................... 540/464
(58) Field of Classification Search ................... 540/464
See application file for complete search history.

(56) References Cited

U.S. PATENT DOCUMENTS

| 3,755,162 A | 8/1973 | Schultz et al. |
| 3,825,532 A | 7/1974 | Kern et al. |

FOREIGN PATENT DOCUMENTS

| GB | 1 467 565 | 3/1977 |
| JP | S51-41376 A | 4/1976 |
| JP | S51-46109 B | 12/1976 |
| JP | S52-12198 B | 4/1977 |
| WO | WO 2007/125002 A1 | 11/2007 |

OTHER PUBLICATIONS

Furuya, Y. et al., "Cyanuric Chloride as a Mild and Active Beckmann Rearrangement Catalyst," Journal of the American Chemical Society, (Jul. 23, 2005), vol. 127, No. 32, pp. 11240-11241.
Zhu, M. et al, "A mild and efficient catalyst for the Beckmann rearrangement," BOP-C1, Tetrahedron Letter, (2006.06.05), vol. 47, No. 28, p. 4861-4863.
International Preliminary Report on Patentability and Written Opinion in corresponding PCT Application No. PCT/JP2009/058018, mailed Dec. 23, 2010.
International Search Report issued in corresponding PCT Application No. PCT/JP2009/054210, mailed Jun. 23, 2009.
International Search Report issued in corresponding PCT Application No. PCT/JP2009/058018, mailed Jun. 23, 2009.
Supplementary European Search Report issued in counterpart European Patent Application No. 09738738.5 on Mar. 2, 2012.
Office Action issued in European Patent Application No. 09738738.5 on Oct. 29, 2012.

*Primary Examiner* — Bruck Kifle
(74) *Attorney, Agent, or Firm* — Knobbe Martens Olson & Bear LLP

(57) ABSTRACT

The present invention relates to a process for producing an amide or lactam, particularly laurolactam, wherein catalytic amounts of an acidic chloride and a Lewis acid are used in Beckmann rearrangement of an oxime compound. In accordance with the process, side reactions during Beckmann rearrangement can be so controlled that selectivity can be improved and strong coloring in the reaction can be prevented, giving a high-quality amide or lactam.

1 Claim, No Drawings

PROCESS FOR PRODUCING AMIDE OR LACTAM

This application is the U.S. National Phase under 35 U.S.C. §371 of International Application PCT/JP2009/058018, filed Apr. 22, 2009, designating the U.S., and published in Japanese as WO2009/133801 on Nov. 5, 2009, which claims priority to Japanese Patent Application No. 2008-120431, filed May 2, 2008; and to Japanese Patent Application No. 2008-227669, filed Sep. 5, 2008, the entire contents of which are incorporated herein by reference.

TECHNICAL FIELD

The present invention relates to a process for producing a lactam or amide useful as a starting material for medical drugs, agricultural chemicals, dyes and polyamides and as a solvent, particularly relates to a process for producing the amide or lactam by a rearrangement reaction of an oxime compound.

Particularly, the present invention relates to a process for producing laurolactam, useful as a starting material for 12-Nylon, by Beckmann rearrangement of cyclododecanone oxime.

BACKGROUND ART

A common industrial process for producing an amide compound involves Beckmann rearrangement of a corresponding oxime compound. For example, ε-caprolactam which is industrially useful is produced by Beckmann rearrangement of cyclohexanone oxime. A rearrangement catalyst is generally concentrated sulfuric acid and oleum, and since these strong acids must be used in the stoichiometric amounts or more, a large amount of ammonium sulfate are formed as a byproduct during neutralization.

There is, therefore, a need for a Beckmann rearrangement catalyst with least environmental impact.

As for producing processes for laurolactam, Patent Reference Nos. 1 and 2 have disclosed that laurolactam is produced by Beckmann rearrangement of cyclododecanone oxime or its hydrochloride using a catalytic amount of, for example, phosphorous trichloride, phosphorous pentachloride, thionyl chloride and sulfuryl chloride. However, in this method, selectivity is inadequate, a reaction product is strongly colored, and product quality is unsatisfactory.

CITATION LIST

Patent Literature

Patent Reference No. 1: Japanese Laid-open Patent application No. S51-41376(1976-41376).
Patent Reference No. 2: Japanese examined patent publication No. S52-12198(1977-12198).
Patent Reference No. 3: Japanese examined patent publication No. S51-46109(1976-46109).

SUMMARY OF INVENTION

Technical Problem

An objective of the present invention is to provide a process for producing a high-quality amide or lactam, particularly laurolactam by a rearrangement reaction of an oxime compound without generating a large amount of byproducts such as ammonium sulfate and with a higher selectivity while suppressing coloring during the reaction.

Solution to Problem

We have found that in producing an amide or lactam by Beckmann rearrangement of an oxime compound using a catalytic amount of an acidic chloride, addition of a Lewis acid can solve the above problems, that is, byproducts are reduced, a selectivity is improved and strong coloring during the reaction is suppressed.

Therefore, the present invention relates to a process for producing an amide or lactam by conducting Beckmann rearrangement of an oxime compound in the presence of an acidic chloride and a Lewis acid to give a corresponding amide or lactam.

Advantageous Effects of Invention

According to the present invention, an amide or lactam, particularly laurolactam can be produced in a high yield and high quality, and an industrially suitable process for producing amide or lactam can be provided.

DESCRIPTION OF EMBODIMENTS

A process for producing an amide or lactam according to the present invention can be conducted by stirring an oxime compound and catalytic amounts of an acidic chloride and a Lewis acid in an organic solvent under heating.

In the present invention, the oxime compound can be appropriately selected, without any particular restriction, depending on the targeted amide or lactam For example, it may be the compound represented by formula (1).

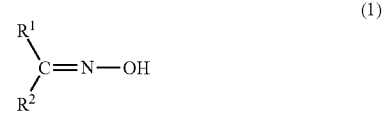

(1)

wherein $R^1$ and $R^2$ represent an organic group respectively, or $R^1$ and $R^2$ together may represent a divalent organic group, whereby forming a ring with a carbon atom to which $R^1$ and $R^2$ attach.

Examples of an organic group as $R^1$ and $R^2$ include alkyl, alkenyl, alkynyl, cycloalkyl, cycloalkenyl, aryl, aralkyl, and aromatic or non-aromatic heterocycle.

Here, alkyl may be, for example, alkyl having 1 to 20, preferably 1 to 12, more preferably 2 to 8 carbon atoms. Specific examples include methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl.

Alkenyl may be, for example, alkenyl having 2 to 20, preferably 2 to 12, more preferably 2 to 8 carbon atoms. Specific examples include vinyl, allyl, 1-propenyl, 1-butenyl, 1-pentenyl and 1-octenyl.

Alkynyl may be, for example, alkynyl having 2 to 20, preferably 2 to 12, more preferably 2 to 8 carbon atoms. Specific examples include ethynyl and 1-propynyl.

Cycloalkyl may be, for example, cycloalkyl having 3 to 20, preferably 3 to 15 carbon atoms. Specific examples include cyclopropyl, cyclobutyl, cyclopentyl, cyclohexyl, cycloheptyl, cyclooctyl and cyclododecyl.

Cycloalkenyl may be, for example, cycloalkenyl having 3 to 20, preferably 3 to 15 carbon atoms. Specific examples include cyclopentenyl, cyclohexenyl and cyclooctenyl.

Examples of aryl include phenyl and naphthyl.

Examples of aralkyl include benzyl, 2-phenylethyl and 3-phenylpropyl.

Examples of aromatic or non-aromatic heterocycle include 2-pyridyl, 2-quinolyl, 2-furyl, 2-thienyl and 4-piperidinyl.

When $R^1$ and $R^2$ together represent a divalent organic group, they form a ring with a carbon atom to which they attach. Examples of such a divalent organic group include straight-chain or branched alkylene groups, preferably straight alkylene groups, and examples of a ring formed include 3- to 30-membered rings, preferably 4- to 20-membered rings, more preferably 5- to 14-membered rings.

These organic groups, whether or not they form a ring, may have various substituents without any particular restriction as long as they do not inhibit the reaction. Examples of a substituent include halogen, oxo, mercapto, substituted oxy (alkoxy, aryloxy, acyloxy and so on), substituted thio, substituted oxycarbonyl, substituted or unsubstituted carbamoyl, cyano, nitro, substituted aminoalkyl, alkenyl, alkynyl, cycloalkyl, cycloalkenyl, aryl (phenyl, naphthyl and so on), aralkyl and heterocycle.

Specific examples of an oxime compound represented by Formula (I) include acetone oxime, 2-butanone oxime, 2-pentanone oxime, 3-pentanone oxime, 1-cyclo hexyl-1-propanone oxime, acetophenone oxime, benzophenone oxime and 4-hydroxyacetophenone oxime, and those forming a ring include cyclopropanone oxime, cyclobutanone oxime, cyclohexanone oxime, cycloheptanone oxime, cyclooctanone oxime, cyclononanone oxime, cyclodecanone oxime, cyclododecanone oxime, cyclotridecanone oxime, cyclotetradecanone oxime, cyclopentadecanone oxime, cyclohexadecanone oxime, cyclooctadecanone oxime and cyclononadecanone oxime.

One oxime compound or two or more oxime compounds may be selected and used.

An oxime compound is prepared by reacting a ketone corresponding to an oxime compound represented by Formula (I) with hydroxylamine. For example, cyclododecanone oxime can be prepared by reacting cyclododecanone with hydroxylamine sulfate as described in Patent Reference No. 3.

Furthermore, it may be also prepared by reacting a compound having a methyl or methylene group with a nitrite ester or nitrite salt in the presence of an N-hydroxyimide compound derived from an aliphatic polycarboxylic anhydride (cyclic anhydride) or an aromatic polycarboxylic anhydride (cyclic anhydride), such as N-hydroxysuccinimide, N-hydroxyphthalic imide, N,N'-dihydroxypyromellitic diimide, N-hydroxyglutarimide, N-hydroxy-1,8-naphthalenedicarboxylic imide and N,N'-dihydroxy-1,8,4,5-naphthalenetetracarboxylic diimide, or a compound prepared by introducing a protective group (for example, an acyl group such as acetyl) into the hydroxyl group in the N-hydroxyimide compound.

This reaction may be conducted in the absence or presence of a solvent. When a solvent is used, there are no particular restrictions to the solvent as long as they do not inhibit the reaction; for example, aromatic hydrocarbons such as benzene, toluene, xylene, cumene and chlorobenzene, aliphatic hydrocarbons such as n-hexane, n-heptane, n-octane, n-nonane, cyclohexane, cyclooctane, cyclodecane, cyclododecane and hydrocumene, ketones such as acetone, methyl ethyl ketone, methyl isopropyl ketone, methyl isobutyl ketone, cyclohexanone and cyclododecanone, nitriles such as acetonitrile, propionitrile and benzonitrile, amides such as formamide, acetamide, N,N-dimethylformamide, N,N-dimethylacetamide, N-methylpyrrolidone and 1,3-dimethyl-2-imidazolinone, sulfoxides such as dimethyl sulfoxide and sulfolane, sulfones, esters such as ethyl formate, methyl acetate, ethyl acetate, butyl acetate, methyl propionate and ethyl butanoate, carboxylic acids such as formic acid, acetic acid, prop ionic acid, butanoic acid and trifluoroacetic acid, ethers such as diethyl ether, diisopropyl ether, tetrahydrofuran and dioxane, phosphoric amides such as hexamethylphosphoric triamide, halogenated hydrocarbons such as chloroform, dichloromethane, dichloroethane, carbon tetrachloride, chlorobenzene and trifluoromethylbenzene, nitro compounds such as nitrobenzene, nitromethane and nitroethane, and fluorinated alcohols such as hexafluoroisopropyl alcohol and trifluoroethanol. Particularly preferred is toluene.

These solvents may be used alone or in combination of two or more.

The amount of a solvent is, but not limited to, generally 0 to 100 times, preferably 1 to 50 times by weight of an oxime compound.

Examples of an acidic chloride include sulfur-containing chlorides such as thionyl chloride, sulfuryl chloride, chlorosulfonic acid, benzenesulfonyl chloride and p-toluenesulfonyl chloride, inorganic phosphorous chlorides such as phosphorous trichloride, phosphorous pentachloride and phosphorous oxychloride, carbonic or carboxylic chlorides such as formyl chloride, acetyl chloride, benzoyl chloride, phosgene and oxalyl chloride, and boric chlorides such as boron trichloride, preferably sulfur-containing chlorides such as thionyl chloride, sulfuryl chloride, chlorosulfonic acid, benzenesulfonyl chloride and p-toluenesulfonyl chloride, particularly preferably thionyl chloride.

The acidic chloride is used in a catalytic amount, that is, 10 mol % or less, preferably 5 to 0.1 mol %, more preferably 3.5 to 0.7 mol % to an oxime compound.

Examples of a Lewis acid include, but not limited to, metal halides such as zinc chloride, iron chloride, cobalt chloride, tin chloride, aluminum chloride and titanium chloride, halogenated boron compounds such as boron trifluoride, and triflate compounds such as yttrium triflate and hafnium triflate. Particularly preferred is zinc chloride.

A Lewis acid is used in a catalytic amount, that is, 10 mol % or less, preferably 5 to 0.1 mol %, more preferably 2.1 to 0.9 mol % to cyclododecanone oxime.

The amount of a Lewis acid to an acidic chloride is 0.01 to 99 mol, preferably 0.1 to 9 mol, more preferably 0.29 to 1.4 mol to 1 mol of acidic chloride.

Even if the amount of a Lewis acid is reduced, the reaction proceeds by increasing the amount of an acidic chloride, but an excessively reduced amount may lead to deterioration in selectivity improving effect and coloring reducing effect.

A combination of an acidic chloride and a Lewis acid is preferably thionyl chloride with zinc chloride, which is significantly effective in Beckmann rearrangement of cyclododecanone oxime.

A reaction temperature may be appropriately selected, depending on factors such as the types of an oxime compound used, a catalyst, a solvent and so on, and is preferably, but not limited to, 20 to 120° C.

There are no particular restrictions to a reaction pressure and the reaction can be conducted under an ambient pressure or under an increased pressure.

The reaction can be conducted under an atmosphere of an inert gas such as nitrogen and argon, and may be conducted in the air or under an oxygen atmosphere.

A reaction time varies depending on the reaction conditions such as the above concentration and a temperature, and may be generally 0.01 to 24 hours, preferably 0.05 to 6 hours.

In the process of the present invention, the oxime compound represented by formula (1) gives an amide compound while a cyclic oxime compound gives a lactam. Specifically, acetophenone oxime gives acetanilide, while cycloalkanone oxime gives a lactam having the ring-member number increased by one.

For example, cyclohexanone oxime gives ε-caprolactam, cycloheptanone oxime gives 7-heptane lactam, cyclooctanone oxime gives 8-octane lactam, and cyclododecanone oxime gives laurolactam At the end of the reaction, a product can be separated and purified by separation means such as filtration, concentration, distillation, extraction, crystallization, recrystallization, adsorption and column chromatography or combinations thereof.

For example, the reaction of cyclododecanone oxime can be worked up by adding water to the mixture, extracting the mixture with an organic solvent and evaporating the solvent to give laurolactam, which can be further separated and purified by, for example, distillation and/or crystallization.

There are no particular restrictions to a reactor, and a reactor equipped with a common stirring apparatus may be used.

EXAMPLES

There will be specifically described the present invention with reference to Examples, but the invention is not limited to these examples. The quantitative analyses of reaction solutions were conducted by gas chromatography with the internal standard method. Thionyl chloride was used as a 10 wt % toluene solution in Examples 1, 2 and Comparative Examples and as a 4.98 wt % toluene solution in Example 4. In Example 3, materials were placed and blended in a reactor without being diluted in a solvent. The amounts of the compounds used in Examples and Comparative Examples are shown in Table 1.

Example 1

A mixture of 1.00 g of cyclododecanone oxime (5.1 mmol), a 10 wt % of thionyl chloride in toluene solution (205 mg, 20.5 mg as thionyl chloride (0.17 mmol)), 7 mg of zinc chloride (0.05 mmol) and 3.8 g of dry toluene was heated with stirring in an oil bath at 95° C. for one hour. The reaction solution was transparent brown, and the quantitative analysis was conducted by gas chromatography with internal standard method (the same analyses were conducted in Examples and Comparable Examples described below); a conversion of cyclododecanone oxime was 99.2% and a yield of laurolactam was 98% (selectivity: 99%).

Example 2

A mixture having the composition shown in Table 1 was heated with stirring in an oil bath at 95° C. for one hour. A reaction solution was transparent brown, and a conversion of cyclododecanone oxime was 99.6% and a yield of laurolactam was 99.6% (selectivity: 100%).

Example 3

A mixture having the composition shown in Table 1 was heated with stirring in an oil bath at 103° C. for one hour. A reaction solution was transparent brown, and a conversion of cyclododecanone oxime was 100% and a yield of laurolactam was 99% (selectivity: 99%).

Example 4

A mixture having the composition shown in Table 1 was heated with stirring in an oil bath at 103° C. for one hour. A reaction solution was transparent brown, and a conversion of cyclododecanone oxime was 100% and a yield of laurolactam was 100% (selectivity: 100%).

Comparative Example 1

A mixture having the composition shown in Table 1 was heated with stirring in an oil bath at 95° C. for one hour. A reaction solution was blackish brown and opaque with less brightness. A conversion of cyclododecanone oxime was 43% and a yield of laurolactam was 35% (selectivity: 81%).

Comparative Example 2

A mixture having the composition shown in Table 1 was heated with stirring in an oil bath at 138° C. for one hour. A reaction solution was blackish brown and opaque with less brightness. A conversion of cyclododecanone oxime was 61% and a yield of laurolactam was 60% (selectivity: 98%).

Comparative Example 3

A mixture having the composition shown in Table 1 was heated with stirring in an oil bath at 95° C. for one hour. A reaction solution was blackish brown and opaque with less brightness. A conversion of cyclododecanone oxime was 100% and a yield of laurolactam was 95% (selectivity: 95%).

TABLE 1

|  | Cyclododecanone oxime (Ox) | Thionyl chloride ($SOCl_2$) | Zinc chloride ($ZnCl_2$) | $SOCl_2$/Ox (mol %) | $ZnCl_2$/Ox (mol %) | $ZnCl_2$/$SOCl_2$ (molar ratio) | Dry toluene |
|---|---|---|---|---|---|---|---|
| Example 1 | 1.00 g (5.1 mmol) | 20.5 mg (0.17 mmol) | 7 mg (0.05 mmol) | 3.3 | 0.98 | 0.29 | 3.8 g |
| Example 2 | 2.01 g (10.2 mmol) | 24.8 mg (0.21 mmol) | 28.8 mg (0.21 mmol) | 2.1 | 2.1 | 1 | 7.8 g |
| Example 3 | 4.53 g (22.9 mmol) | 21.7 mg (0.18 mmol) | 31.8 mg (0.23 mmol) | 0.79 | 1 | 1.28 | 10.5 g |
| Example 4 | 4.53 g (23.0 mmol) | 20.3 mg (0.17 mmol) | 31.7 mg (0.23 mmol) | 0.74 | 1 | 1.35 | 10.7 g |
| Comparative Example 1 | 1.00 g (5.1 mmol) | 20.5 mg (0.17 mmol) | — | 3.3 | — | — | 3.8 g |

TABLE 1-continued

|  | Cyclododecanone oxime (Ox) | Thionyl chloride (SOCl$_2$) | Zinc chloride (ZnCl$_2$) | SOCl$_2$/Ox (mol %) | ZnCl$_2$/Ox (mol %) | ZnCl$_2$/SOCl$_2$ (molar ratio) | Dry toluene |
|---|---|---|---|---|---|---|---|
| Comparative Example 2 | 1.01 g (5.1 mmol) | 20.4 mg (0.17 mmol) | — | 3.3 | — | — | 4.7 g |
| Comparative Example 3 | 1.03 g (5.1 mmol) | 30.2 mg (0.25 mmol) | — | 4.9 | — | — | 4.7 g |

What is claimed is:

1. A process for producing laurolactam, comprising conducting Beckmann rearrangement of cyclododecanone oxime in the presence of thionyl chloride and zinc chloride.

* * * * *